April 18, 1961 F. W. ANDERSON Plant Pat. 2,049
PLUM TREE
Filed July 18, 1960
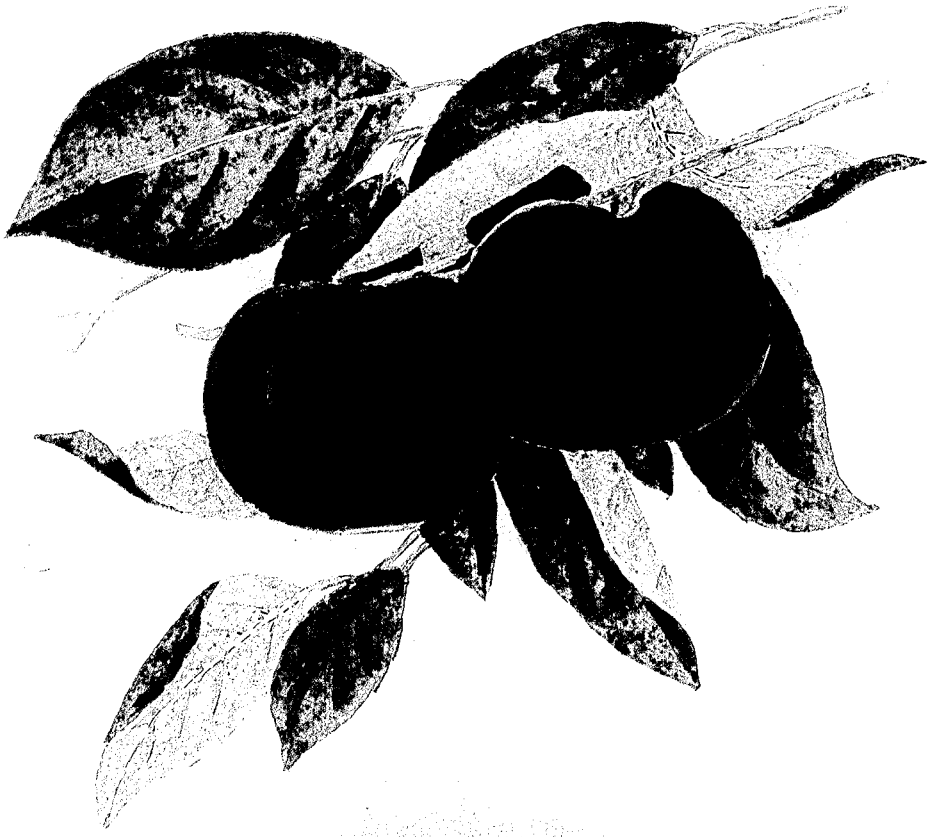
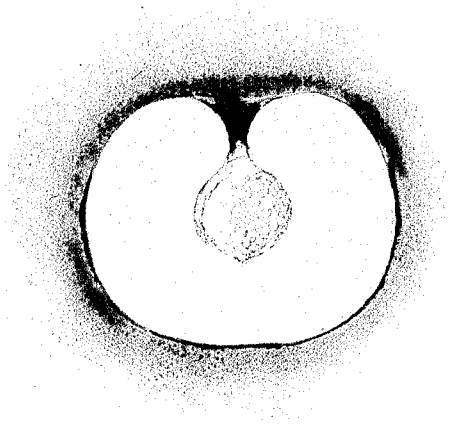
WITNESS
Addison E. Avery
INVENTOR
Frederic W. Anderson
Webster & Webster
ATTYS.

United States Patent Office

Plant Pat. 2,049
Patented Apr. 18, 1961

2,049

PLUM TREE

Frederic W. Anderson, Merced, Calif., assignor to Kim Bros., doing business as Reedley Nursery, Reedley, Calif., a copartnership Filed July 18, 1960, Ser. No. 43,698

1 Claim. (Cl. 47—62)

The present invention relates to a new and distinct variety of plum tree which bears large, globose to oblate, semi-freestone fruit having yellow flesh and a deep blue exterior color with a slight grey bloom.

As compared with the El Dorado plum (unpatented) the fruit of the present variety—while similar in color, firmness, eating quality, and a slightly rough skin texture—is distinctively characterized by at least half again larger size, and by coloring and ripening at least one week earlier.

As compared with the Santa Rosa plum (unpatented) the fruit of the present variety is larger, firmer, blue instead of dark red exterior color, better withstands long distance shipping, keeps for a longer time, and—although coloring at substantially the same time—is harvested somewhat later.

The herein claimed variety of plum tree was originated by me, in my experimental orchard located near Merced, California, as a selected seedling from a large number thereof obtained from El Dorado plum seeds that had originated from open-pollinated flowers.

Such large number of seedlings, which were grown under careful observation by me, reflected—when they came into bearing—many and varying characteristics; one of said seedlings, and which is the present variety, having been especially desirable with respect to its fruit characteristics, and I therefore selected such seedling for asexual reproduction and commercialization.

Subsequent to its origination and selection by me, asexual reproduction of the variety was successfully accomplished by topworking on mature nectarine trees in my experimental orchard located as aforesaid; the reproductions having run true to the parent in every respect.

In the drawings:

Fig. 1 is an elevation showing two of the plums, together with a twig and leaves.

Fig. 2 is a sectional elevation of one of the plums, with the stone remaining in place.

Referring now more specifically to the pomological details of this new and distinct variety of plum tree, the following is an outline description thereof; all major color plate identifications being by reference to Maerz and Paul Dictionary of Color, except where otherwise indicated or where common terms of color definition are employed.

Tree:
- *Size.*—Large.
- *Vigor.*—Vigorous.
- *Form.*—Spreading.
- *Production.*—Productive.
- *Bearing.*—Regular bearer.

Trunk:
- *Size.*—Medium.
- *Bark.*—Smooth.

Branches:
- *Size.*—Medium.
- *Bark.*—Smooth.

Leaves:
- *Size.*—Medium. Average length—3". Average width—1½".
- *Thickness.*—Medium.
- *Texture.*—Smooth.
- *Margin.*—Crenate.
- *Petiole.*—Medium length; medium thickness.
- *Glands.*—Average number and position usually two or three on petiole near base of blade. Alternate; small.
- *Color.*—Top side—medium green (23–L–7). Under side—lighter green (21–A–6).

Flower buds:
- *Size.*—Medium to small.
- *Length.*—Medium.
- *Form.*—Conic.

Flowers:
- *Blooming period.*—Approximately with the Santa Rosa. Medium as compared with other varieties.
- *Color.*—White.

Fruit:
- *Maturity when described.*—Eating ripe, July 20, 1959.
- *Date of first picking.*—July 1, 1959.
- *Date of last picking.*—July 20, 1959.
- *Size.*—Uniform; large. Average diameter axially—2⅛". Average transversely in suture plane—2¼".
- *Form.*—Uniform; symmetrical; globose to oblate.
- *Suture.*—Distinct; extends from base to apex.
- *Ventral surface.*—Rounded strongly.
- *Cavity.*—Average depth—⅜". Average breadth—¾".
- *Base.*—Rounded.
- *Apex.*—Rounded to flat.

Skin:
- *Thickness.*—Medium.
- *Texture.*—Tough.
- *Tenacity to flesh.*—Tenacious.
- *Tendency to crack.*—None.
- *Down.*—Wanting.
- *Color.*—Deep purple-blue (Aconite violet—British Colour Council Horticultural Colour Chart, Plate 937). Slight grey bloom.

Flesh:
- *Juice.*—Abundant.
- *Texture.*—Firm; meaty; melting.
- *Ripens.*—Even.
- *Fibers.*—Few.
- *Flavor.*—Delicate; vinous.
- *Eating quality.*—Good to best.
- *Color.*—Yellow (10–G–3) near stone, shading darker (11–I–6 to 11–G–7) towards skin.

Stone:
- *Type.*—Semi-free.
- *Size.*—Small. Average length—¾". Average breadth—11/16". Average thickness—3/16".
- *Form.*—Globose.
- *Base.*—Straight.
- *Apex.*—Rounded.
- *Sides.*—Equal.
- *Ventral edge.*—Thin.
- *Dorsal edge.*—Narrow, with shallow groove.
- *Ridges.*—Continuous.
- *Tendency to split.*—None.
- *Color.*—Cream-yellow (10–F–4), shading in part to light red (1–H–10).

Use: Market; long distance shipping.

Keeping quality: Good.

Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of plum tree, as illustrated and described, which bears large, globose to oblate semi-freestone fruit having yellow flesh and a deep blue exterior color with a slight grey bloom; said fruit—in comparison with the El Dorado—being similar in color, firmness, eating quality, and a slightly rough skin texture, but distinctively characterized by at least half again larger size, and by coloring and ripening at least one week earlier; and—in comparison with the Santa Rosa—by fruit which is larger, firmer, blue instead of dark red exterior color, better withstands long distance shipping, keeps for a longer time, and—although coloring at the same time—is harvested somewhat later.

No references cited.